(12) United States Patent
Weinberg

(10) Patent No.: US 6,376,537 B1
(45) Date of Patent: Apr. 23, 2002

(54) CANCER TREATMENT

(76) Inventor: Assa Weinberg, 1845 Loma Vista, Beverly Hills, CA (US) 90210

( * ) Notice: Subject to any disclaimer, the term of this patent is extended or adjusted under 35 U.S.C. 154(b) by 0 days.

(21) Appl. No.: 09/536,911

(22) Filed: Mar. 28, 2000

(51) Int. Cl.⁷ .............................................. A61K 31/35
(52) U.S. Cl. ..................................................... 514/460
(58) Field of Search ......................................... 514/460

(56) References Cited

U.S. PATENT DOCUMENTS 6,040,334 A * 3/2000 Myers et al. ................ 514/460

OTHER PUBLICATIONS

Carter et al., Chemotherapy of Cancer, second ed., John Wiley & Sons, N. Y., N. Y., pp. 262–263, August 1981.*

* cited by examiner

Primary Examiner—Jerome D. Goldberg
(74) Attorney, Agent, or Firm—Thomas M. Freiburger

(57) ABSTRACT

Simvastatin, a known anti-cholesterol drug, is used in effective doses over a period of time to reduce and sometimes cure cases of advanced malignant solid tumor. Examples of treatment of hepatocellular carcinoma and diffused metastatic colon carcinoma are described.

4 Claims, No Drawings

CANCER TREATMENT

BACKGROUND OF THE INVENTION

This invention concerns a treatment for cancer using a drug administered orally.

In spite of substantial advances in the understanding of the mechanism of oncogenesis (transformation of a normal cell into a malignant one), the treatment of advanced state solid tumor remains elusive. Patients affected with these diseases are destined to die within weeks or months.

Multiple clinical trials could only portray the grim prognosis of patients affected with such diseases as metastatic diffused colon cancer or metastatic diffused liver cancer. Even with the combined use of the four classic treatment modalities: surgery, radiation, chemotherapy and immunotherapy, little has changed over the last five years to alter the deathly outcome. Nothing illustrates this more than the national statistics of hepato-billiary cancer with 15,400 new tumors diagnosed each year and 12,300 annual death rate.

Cancer of the liver of hepatocellular carcinoma is a particular case in point. It is an aggressive and uniformly rapid disease once the spread is beyond the liver. Most patients die within several months. Similar effects are seen in patients with diffused colon cancer. Once the disease progresses or cannot be halted beyond the bowel wall, it is uniformly, rapidly fatal within months and no known cure or prolongation of life regimen is currently known.

SUMMARY OF THE INVENTION

The invention described herein is a new model treatment for advanced malignant solid tumor. In particular, hepatocellular carcinoma and diffused metastatic colon carcinoma.

The new treatment consists of the oral administration of high dose Simvastatin, a well-known anti-cholesterol drug marketed by Merck but whose anti-cancer property has never been previously known. Because of ethical considerations, treatment under the scope of this invention has been offered only to terminally ill patients with disease status which was considered by the patients' oncology experts to be hopeless.

Using such treatment, previously unobtainable clinical results, remission or cure has been obtained in these hopeless cases.

These and other objects, advantages and features of the invention will be apparent from the following description of a preferred embodiment, considered along with the accompanying drawings.

DESCRIPTION OF PREFERRED EMBODIMENTS

THE DRUG

Simvastatin is a cholesterol-lowering agent that is derived synthetically from a fermentation product of Aspergellus Ferrous. It has been used extensively in the treatment of hyperlipidermia and its pharmacology and toxicology are well-known.

Its use according to this invention in the treatment of malignant disease consists of daily administration of an 80 mg tablet orally. Patients who underwent this treatment with terminal metastatic colon cancer achieved a life expectancy of several years over that previously described. In the case of diffused metastatic liver cancer, an apparent cure was achieved.

METHOD OF TREATMENT

In order to avoid unforeseen side effects, the treatment is initiated at about 20 mg dose tablet once daily for one week. The dose then is increased to about 40 mg once daily for an additional week. The following week the dose is increased to about 60 mg and on the fourth week the dose is increased to about 80 mg (two tablets of 40 mg each), and to remain so indefinitely. The intervals for stepping up the dosage can vary.

CLINICAL RESULTS

Due to the non-toxic nature of the drug, there is no need for hospitalization, frequent laboratory tests or administration of intravenous medication. In one case the patient went for several months on vacation in another state, remaining only in telephone contact while continuing to take the drug.

The first results are seen in several months, initially manifested by the persistent survival of the patient. In the case of colon cancer treatment, the results manifest by progressive improvement of health status including nutritional and functional status to normal or near normal.

In the case of liver cancer the first indication of recovery is marked by rapid decline of the tumor marker, alpha fetoprotein, to normal level, followed by improvements in liver function tests, then followed by regression of the tumor and its metastasis.

In this case of liver cancer as reported below, no evidence of persistent malignant process can be demonstrated, by the time of this description and filing.

Case Reports, Experimental Treatments With This Drug

Liver Cancer Case 70-year-old lady was admitted to Cedars Sinai Medical Center in Los Angeles because of left humeral fracture for malignant metastatic disease. Subsequent studies revealed that she had a large mass in her liver with multiple nodular spread to the abdominal cavity and both adrenal glands. She underwent laparotomy and biopsy which identified the liver mass as hepatocellular carcinoma. The tumor marker, alpha fetoprotein, was above 55,000. She was bedridden, weak, in severe pain and required frequent administration of narcotic analgesic. A liver specialist found her to be beyond possible rescue by any therapeutic means. She was started on Simvastatin in January of 1999. By April of 1999 her alpha fetoprotein was less than 8, and it is 2.4 in March 2000.

Her liver mass progressively declined in size. Her first adrenal mass resolved by June of 1999, and the second by March 2000. Her humeral fracture completely healed. She required no further narcotic analgesics. Her nutritional status and functional capacity returned to normal. At the present time, no cancer can be detected by any imaging studies: MRI, CT Scan, ultrasound or radio nucleotide scan. At the time of this description, she appears to be free of malignant disease.

Colon Cancer

Case #1: 65-year-old business man who underwent hemicolectomy for adenocarcinoma of the colon in 1993 was presented in 1995 to Cedars Sinai Medical Center Liver Team for possible cryotherapy. At that time he had multiple masses in both lobes of the liver as well as outside his liver and multiple nodules in both lungs. Clinically he was bedridden, weak and malnourished. He was rejected as a suitable candidate for needle cryotherapy because of his advanced disease, and was considered unrescuable with a life expectancy of several weeks.

He was started on a 20 mg dose of Simvastatin daily in March of 1995. The dose was increased by 20 mg increments every two weeks up to the dose of 80 mg. Over the next three to four months his liver function tests improved and his functional capacity was amazingly restored to normal. He gained 27 pounds, became normally active, including extensive travel around the world.

Imaging studies of his liver revealed that many, but not all, of his liver metastasis completely resolved. He remained stable for several years and succumbed to his disease four years later.

Case #2: 68-year-old lady underwent hemicolectomy for cancer of the colon in 1995 because of intestinal obstruction. During the surgery, she was found to have multiple liver and lung metastasis and refused any further treatment. Oncology consultation found her beyond rescue with a life expectancy of several months. She was transferred to a nursing home where she was bedridden, malnourished and totally dependent. She was started on Simvastatin in 1995. Within several months she regained weight and strength, associated with improvement in liver function tests. She became completely independent and ambulatory. She remained completely functional for the next several years and died of pneumonia in November of 1999.

Case #3: 90-year-old retired artist with metastatic liver disease of colon carcinoma was seen because of rapid weight loss, decline in functional status and jaundice. Because of his advanced age, he refused any standard oncological intervention but agreed to take Simvastatin. His weight has progressively increased, as well as his energy level. His liver function test and jaundice markedly improved. He became independent and ambulatory and still performs sculpturing, now several months after initiation of the treatment.

POSSIBLE MECHANISM OF ACTION

Even though no direct experiments were conducted to establish the cellular mechanism by which Simvastatin caused the regression or the cure in the abovementioned malignant diseases, the similarity in the response in all these cases, and the progressive mode of the improvement, enable drawing some insights into such mechanism.

The first observation is the gentle nature of the therapeutic response. In all the patients the clinical improvement was easily obtained without any dramatic event or any decline in clinical status. The treatment course did not require any special supervision or special diagnostic tests. No evidence of events such as tumor lysis syndrome of deterioration in general health, which are associated with rapid death of tumors, were ever noted.

The second observation was that in all cases improvement was progressive and lasted many months to many years. The decline in tumor burden was slow. It requires many months to be achieved, and has been heralded by progressive, rather than sudden clinical improvement. The biological and radiological improvement followed the same rule. However, patient improvement is persistent even while evidence of the tumor still exists.

The observation that the tumor marker, alpha fetoprotein, normalized completely prior to the reduction in tumor mass is of capital importance. As currently used by oncologists, a reduction in the level of the liver cancer tumor marker can only be achieved by reduction in tumor mass. If an elevated alpha fetoprotein test normalized after surgical resection of liver cancer, it is currently thought as complete eradication of the tumor by surgery. The opposite is also true if the test remains high after surgical resection. It will indicated that not all tumor cells were removed. Hence the name "tumor marker".

The observation in the case here presented, the liver cancer case, gives an insight of completely different significance. In that case, the tumor marker completely normalized prior to the reduction in tumor mass, several months after the initiation of Simvastatin treatment. Alpha fetoprotein is a gene product associated with the malignant process of hepatocellular carcinoma. The normalization of this test indicates that Simvastatin interferes with the malignant program of the cancer cell at its genetic level. This interventional process appears to be a new therapeutic approach to the treatment of malignant disease: a reverse oncogenesis.

The gentle and prolonged improvement in the clinical status of all patients is further indication of the nature of this process. It renders highly unlikely that Simvastatin kills cancer cells while leaving intact normal cells. The malignant transformation of cells was considered until now an irreversible process.

The ability of Simvastatin to interfere with this process reveals another property of the treatment: the prevention of malignant formation by normalizing the genetic alteration that leads to malignancy. By normalizing the genetic alteration Simvastatin is able to prevent the formation of solid tumors or to slow their appearance. In the case of hepatocellular carcinoma, this reversal is apparently complete; in the case of colon cancer, the reversal is incomplete, but leads to a major delay in the progression of colon cancer metastasis.

This is a completely new approach to the treatment and management of malignant diseases. All the currently available methods for the treatment of malignancy, without exception, are based in the selective killing of malignant cells. These methods are resection, radiation, chemotherapy and immunotherapy. Simvastatin and similarly operating substances open the way for a completely new mode of treatment: reversal of genetic processing of malignancy, a revolutionary method with curative and preventive capabilities.

It logically can be extrapolated from the above test results that Simvastatin in the dose listed above can improve or cure other malignant solid tumors, including breast, lung, esophagus, pancreas, gastric, kidney and adrenal. Also, because of the nature of the results as described, it can be assumed that Simvastatin can prevent the appearance of malignant disease in specifically prone subgroups of patients such as carriers of hepatitis B and C virus, and patients with family history of malignant bowel disease. Also, it can prevent or reduce the incidence of malignant mesenchymal tumors in the normal population.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A method for treating hepatocellular carcinoma of the liver in a human patient, comprising treating the patient with an effective oral dosage of simvastatin, over a period of time effective to reduce or eliminate tumor burden.

2. The method of claim 1, wherein the treatment dosage is about 20 mg to about 80 mg daily dosage.

3. The method of claim 2, including initially treating the patient with approximately 20 mg daily dose of simvastatin, and stepping up the dosage over successive periods of at least one week until the dosage reaches about 80 mg daily.

4. A method for preventing the appearance of hepatocellular carcinoma of the liver in human patients, comprising treating the patient in need thereof with about 20 mg to about 80 mg daily dosage orally of simvastatin.

* * * * *